US006534630B1

(12) United States Patent
Li et al.

(10) Patent No.: US 6,534,630 B1
(45) Date of Patent: *Mar. 18, 2003

(54) CONNECTIVE TISSUE GROWTH FACTOR-2

(75) Inventors: Haodong Li, Gaithersburg, MD (US); Mark D. Adams, North Potomac, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/348,815

(22) Filed: Jul. 8, 1999

Related U.S. Application Data

(62) Division of application No. 08/459,101, filed as application No. PCT/US94/07736 on Jul. 12, 1994, now Pat. No. 5,945,300.

(51) Int. Cl.[7] .......................... C07K 1/00; A61K 38/00; C12Q 1/68; C12P 21/06; C12P 21/04

(52) U.S. Cl. ........................ 530/350; 435/6; 435/455; 435/69.1; 435/69.7; 530/300

(58) Field of Search ..................... 530/300, 350; 435/69.1, 70.1, 325

(56) References Cited

U.S. PATENT DOCUMENTS

| | | |
|---|---|---|
| 5,408,040 A | 4/1995 | Grotendorst et al. |
| 5,792,453 A | 8/1998 | Hammond et al. |
| 5,837,258 A | 11/1998 | Grotendorst |
| 5,944,710 A | 8/1999 | Dev et al. |
| 6,051,424 A | 4/2000 | Kato et al. |

FOREIGN PATENT DOCUMENTS

| | | |
|---|---|---|
| EP | 0495674 | 7/1992 |
| EP | 495 674 A2 * | 7/1992 |
| WO | WO 88/03409 | 5/1988 |
| WO | WO 89/08667 | 9/1989 |
| WO | WO 94/03599 | 2/1994 |
| WO | WO 97/33995 | 9/1997 |
| WO | WO 00/35939 | 6/2000 |

OTHER PUBLICATIONS

Timothy P. O'Brien et al., Expression of cyr61, a Growth Factor–Inducible Immediate–Early Gene; Molecular and Cellular Biology, Jul. 1990, pp. 3569–3577.*

Branko V. Latinkic et al., Promoter function and structure of the growth factor–inducible immediate early gene cyr61; Nucleic Acids Research, 1991, vol. 19, No. 12 pp. 3261–3267.*

U.S. patent application No. 09/912,293, Rosen et al., file not published.

Geneseq Accession No. AAT97142, Toyobo, K.K., "Human monocyte mature differentiation factor encoding cDNA" (Mar. 5, 1998).

Geneseq Accession No. AAW35957, Toyobo, K.K., "a monocyte mature differentiation factor—useful for the long term tissue culture of macrophase(s)" (Mar. 5, 1998).

Geneseq Accession No. AAT94699, Lau, L.F., "Human cysteine rich protein 61 (Cyr61)cDNA" (Mar. 27, 1998).

Geneseq Accession No. AAW35730, Lau, L.F., "Human cysteine rich protein 61 (Cyr61)" (Mar. 27, 1998).

International Search Report for PCT/US01/21799.

Latinkic et al., *Nucleic Acids Research*, 19(12):3261–3267 (1991).

O'Brien et al., *Molecular and Cellular Biology*, 10(7):3569–3577 (1990).

Simmons et al., *Proc. Natl. Acad. Sci. USA*, 86:1178–1182 (1989).

Oemar et al., *Hyertension*, 22(3):424 (1993).

Oemar et al., *European Heart Journal*, 15(Abstr. Suppl.):486 (1994).

Bradham et al., *Journal of Cell Biology*, 114(6):1285–1294 (1991).

George et al., "Current methods in sequence comparison and analysis," in *Macromolecular Sequencing and Synthesis, Selected Methods and Applications*, D.H. Schlesinger (ed.), Alan R. Liss, Inc., New York, NY, pp. 127–149 (1988).

Boswell et al., "Sequence Comparison and alignment: the measurement and interpretation of sequence similarity," in *Computational Molecular Biology: Sources and Methods for Sequence Analysis*, Arthur M. Lesk (ed.), Oxford University Press, New York, NY, pp. 161–178 (1988).

O'Brien et al., "Expression of the growth factor–inducible immediate early gene cyr61 correlates with chondrogenesis during mouse embryonic development," in *Cell Growth Differ.*, 3(9):645–654 (Sep. 1992).

GeneSeq Accession No. Q26421 (Jan. 18, 1993).
GeneSeq Accession No. Q26422 (Jan. 18, 1993).
GeneSeq Accession No. R25565 (Jan. 18, 1993).
GeneSeq Accession No. R25566 (Jan. 18, 1993).
GeneSeq Accession No. R46078 (Oct. 19, 1994).
GeneSeq Accession No. Q57417 (Oct. 19, 1994).

* cited by examiner

*Primary Examiner*—Sean McGarry
*Assistant Examiner*—Jane Zara
(74) *Attorney, Agent, or Firm*—Human Genome Sciences, Inc.

(57) ABSTRACT

The present invention relates to a human CTGF-2 polypeptide and DNA (RNA) encoding such polypeptide. Also provided is a procedure for producing such polypeptide by recombinant techniques and antibodies and antagonist/inhibitors against such polypeptide. Also provided are methods of using the polypeptide therapeutically for enhancing the repair of connective and support tissue, promoting the attachment, fixation and stabilization of tissue implants and enhancing wound healing. Diagnostic assays for identifying mutations in nucleic acid sequence encoding a polypeptide of the present invention and for detecting altered levels of the polypeptide of the present invention are also disclosed.

37 Claims, 5 Drawing Sheets

```
ATGAGCTCCCGAATCGTCAGGGAGCTCGCCTTAGTCGTCACCCTTCTCCACTTGACCAGG
 M  S  S  R  I  V  R  E  L  A  L  V  V  T  L  L  H  L  T  R

GTGGGGCTCTCCACCTGCCCCGCTGACTGCCACTGCCCCTGGAGCGCCCAAGTGCGCG
 V  G  L  S  T  C  P  A  D  C  H  C  P  L  E  A  P  K  C  A

CCGGGAGTCGGGGCTGGTCCGGGACGGCTGCGCGTGTTGTAAGGTCTGCGCAAGCAGCTC
 P  G  V  G  L  V  R  D  G  C  G  C  K  V  C  A  K  Q  L

AACGAGGACTGCAGAAAAACGCAGCCCTGCGACCACACCAAGGGCTGAATGCAACTTC
 N  E  D  C  R  K  T  Q  P  C  D  H  T  K  G  L  E  C  N  F

GGCGCCAGCTCCACCGCTCTGAAGGGATCTGCAGAGCTCAGTCAGAGGGCAGACCCTGT
 G  A  S  S  T  A  L  K  G  I  C  R  A  Q  S  E  G  R  P  C

GAATATAACTCCAGAATCTACCAAAACGGGAAAGTTTCCAGCCCAACTGTAAACATCAG
 E  Y  N  S  R  I  Y  Q  N  G  E  S  F  Q  P  N  C  K  H  Q

TGCACATGTATTGGATGGGCGCCGGGGCTTGCATTCCTCTGTGTCCCAAGAACTATCT
 C  T  C  I  G  W  R  R  G  A  C  I  P  L  C  P  Q  E  L  S

CTCCCCAACTTGGGCTGTCCCAACCCTCGGCTGGTCAAAGTTACCGGGCAGTGCTGCGAG
 L  P  N  L  G  C  P  N  P  R  L  V  K  V  T  G  Q  C  C  E
 MATCH WITH FIG.1B
```

FIG. 1A

MATCH WITH FIG.1A

GAGTGGGTCTGTGACGAGGATAGTATCAAGGACCCCATGGAGGACCAGGACGGCCTCCTT
E  W  V  C  D  E  D  S  I  K  D  P  M  E  D  Q  D  G  L  L

GGCAAGGGGCTGGGATTCGATGCCTCCGAGGTGGAGTTGACGAGAAACAATGAATTGATT
G  K  G  L  G  F  D  A  S  E  V  E  L  T  R  N  N  E  L  I

GCAGTTGGAAAAGGCAGCTCACTGAAGCGGCTCCCTGTTTTTGGAATGGAGCCTCGCATC
A  V  G  K  G  S  S  L  K  R  L  P  V  F  G  M  E  P  R  I

CTATACAACCCCTTTACAAGGCCAGAAATGTATTGTTCAAACAACTTCATGGTCCCAGTGC
L  Y  N  P  L  Q  G  Q  K  C  I  V  Q  T  T  S  W  S  Q  C

TCAAAGACCTGTGGAACTGGTATCTCCACACGAGTTACCAATGACAACCCTGAGTGCCGC
S  K  T  C  G  T  G  I  S  T  R  V  T  N  D  N  P  E  C  R

CTTGTGAAAGAAACCCGGATTCTGAGGTGCGGCCTTGTGGACAGCCAGTGTACAGCAGC
L  V  K  E  T  R  I  C  E  V  R  P  C  G  Q  P  V  Y  S  S

CTGAAAAAGGGCAAGAAATGCAGCAAGACCAAGAAATCCCCGAACCAGTCAGGTTTACT
L  K  K  G  K  K  C  S  K  T  K  K  S  P  E  P  V  R  F  T
MATCH WITH FIG.1C

FIG.1B

MATCH WITH FIG. 1B

TACGCTGGATGTTTGAGTGTGAAGAAATACCGGCCCAAGTACTGCGGTTCCTGCGTGGAC
 Y  A  G  C  L  S  V  K  K  Y  R  P  K  Y  C  G  S  C  V  D

GGCCGATGCTGCACGCCCCAGCTGACCAGGACTGTGAAGATGCGGTTCCCTGCGAAGAT
 G  R  C  C  T  P  Q  L  T  R  T  V  K  M  R  F  P  C  E  D

GGGGAGACATTTTCCAAGAACGTCATGATGATCCAGTCCTCCAAATGCAACTACAACTGC
 G  E  T  F  S  K  N  V  M  M  I  Q  S  S  K  C  N  Y  N  C

CCGCATGCCAATGAAGCAGCGGTTTCCCTTCTACAGGCTGTTCCAATGA
 P  H  A  N  E  A  A  F  P  F  Y  R  L  F  Q  *

FIG. 1C

1   MSSRIVRELALVVTLLHLTRVGLSTCPADCHCPLEAPKCAPGVGLVRDGC   50
    |||  |  || ||||||||||||| || ||||||||||||||||||||||
1   MSSSTFRTLAVAVTLLHLTRLALSTCPAACHCPLEAPKCAPGVGLVRDGC   50

51  GCCKVCAKQLNEDCRKTQPCDHTKGLECNFGASSTALKGICRAQSEGRPC   100
    ||||||||||||||| |||||||||||||||||||||||||||||||||
51  GCCKVCAKQLNEDCSKTQPCDHTKGLECNFGASSTALKGICRAQSEGRPC   100

101 EYNSRIYQNGESFQPNCKHQCTCIGWRRGACIPLCPQELSLPNLGCPNPR   150
    MATCH WITH FIG. 2B

FIG. 2A

```
                          MATCH WITH FIG.2A
101  EYNSRIYQNGESFQPNCKHQCTCID.GAVGCIPLCPQELSLPNLGCPNPR     149
151  LVKVTGQCCEEWVCDEDSIKDPMEDQDGLLGKGLGFDASEVELTRNNELI     200
150  LVKVSGQCCEEWVCDEDSIKDSLDDQDDL....LGLDASEVELTRNNELI     195
201  AVGKGSSLKRLPVFGMEPRILYNPL...QGQKCIVQTTSWSQCSKTCGTGI    248
196  AIGKGSSLKRLPVFGTEPRVLFNPLHAHGQKCIVQTTSWSQCSKSCGTGI     245
249  STRVTNDNPECRLVKETRICEVRPCGQPVYSSLKKGKKCSKTKKSPEPVR     298
246  STRVTNDNPECRLVKETRICEVRPCGQPVYSSLKKGKKCSKTKKSPEPVR     295
299  FTYAGCLSVKKYRPKYCGSCVDGRCCTPQLTRTVKMRFPCEDGETFSKNV     348
296  FTYAGCSSVKKYRPKYCGSCVDGRCCTPLQTRTVKMRFRCEDGEMFSKNV     345
349  MMIQSSKCNYNCPHANEAAFPFYRLFQ                            375
346  MMIQSCKCNYNCPHPNEASFRLYSLFN                            372
```

FIG.2B

```
  1  MSSRIVRELALVVTLLHL.TRVGLS.TCPADCHCPLE.APKCAPGVGLVR                                              47
       :|:::||:||||:||::|||||:.|||:|||||:.||:|||||:|:||
  1  MLASVAGPISLALVLLALCTRPATGQDCSAQCQCAAEAAPHCPAGVSLVL                                              50

48  DGCGCCKVCAKQLNEDCRKTQPCDHTKGLECNFGASSTALKGICRAQSEG                                              97
       |||||||:||||||:||:|:|||:|||.|||:||||:|||                          
 51  DGCGCCRVCAKQLGELCTERDPCDPHKGLFCDFGSPANRKIGVCTAK.DG                                              99

98  RPCEYNSRIYQNGESFQPNCKHQCTCIGWRRGACIPLCPQELSLPNLGCP                                             147
       :|:::||:||:|||||:::|||::|||:|:|||:|||
100  APCVFGGSVYRSGESFQSSCKYQCTCLD.GAVGCVPLCSMDVRLPSPDCP                                             148

148  NPRLVKVTGQCCEEWVCDEDSIKDPMEDQDGLLGKGLGFDASEVELTRNN                                             197
       |:|::||||:|:|||:|||
149  FPRRVKLPGKCCKEWVCDEPKDRTAV..........GPALAAYRLEDT...                                            186

198  ELIAVGKGSSLKRLPVFGMEPRILYNPLQGQKCIVQTTSWSQCSKTCGTG                                             247
                       ::||||.....RANCLVQTTEWSACSKTCGMG
187  .................FGPDPTMM.....RANCLVQTTEWSACSKTCGMG                                            215

248  ISTRVTNDNPECRLVKETRICEVRPCGQPVYSSLKKGKKCSKTKKSPEPV                                             297
       ||||||||:|:|||:|||:|||:|:||||||:||:|||
216  ISTRVTNDNTFCRLEKQSRLCMVRPCEADLEENIKKGKKCIRTPKIAKPV                                             265

298  RFTYAGCLSVKKTRPKYCGSCVDGRCCTPQLTRTVKMRFPCEDGETFSKN                                             347
       :|::||||:|:|||::|||||:||||||:|:||
266  KFELSGCTSVKTTRAKFGGVCTDGRCCTPHRTTTLPVEFKCPDGEIMKKN                                             315

348  VMMIQSSKCNYNCPHANE..AAFPFYRLFQ                                                                 375
       :|::|:||:||||:|:||
316  MMFIKTCACHYNCPGDNDIFESLYYRKMYG                                                                 345
```

FIG.3

CONNECTIVE TISSUE GROWTH FACTOR-2

This application is a divisional of U.S. patent application Ser. No. 08/459,101, filed Jun. 2, 1995, now U.S. Pat. No. 5,945,300, which is a continuation-in-part of, and claims priority under 35 U.S.C. §120 to, U.S. Patent Application Ser. No. PCT/US94/07736, filed Jul. 12, 1994, both of which are incorporated herein by reference in their entireties.

This invention relates to newly identified polynucleotides, polypeptides encoded by such polynucleotides, the use of such polynucleotides and polypeptides, as well as the production of such polynucleotides and polypeptides. More particularly, the polypeptide of the present invention is connective tissue growth factor-2 sometimes hereinafter referred to as "CTGF-2". The invention also relates to inhibiting the action of such polypeptides.

The CTGF polypeptides are structurally and functionally related to a family of growth factors which include IGF (insulin-like growth factor), PDGF (platelet-derived growth factor), and FGF (fibroblast growth factor). This emerging family of secreted proteins are a group of cysteine-rich proteins. This group of growth factors are important for normal growth, differentiation, morphogenesis of the cartilaginous skeleton of an embryo and cell growth. Among some of the functions that have been discovered for these growth factors are wound healing, tissue repair, implant fixation and stimulating increased bone mass.

The extended superfamily of growth factors include TGF (transforming growth factor), bone morphogenic factors, and activins, among others.

The most well-known growth factor, TGF exerts a number of different effects on a variety of cells. For example, TGF-β can inhibit the differentiation of certain cells of mesodermal origin (Florini, J. R. et al., *J. Biol. Chem.*, 261:1659–16513 (1986) induced the differentiation of others (Seyedine, S. M. et al., *PNAS USA*, 82:2267–2271 (1987) and potently inhibit proliferation of various types of epithelial cells, (Tucker, R. F., *Science*, 226:705–705 (1984)). This last activity has led to the speculation that one important physiological role for TGF-β is to maintain the repressed growth state of many types of cells. Accordingly, cells that lose the ability to respond to TGF-β are more likely to exhibit uncontrolled growth and become tumorigenic.

Accordingly, due to amino acid sequence homology the polypeptide of the present invention is a member of this extended family of growth factors which has many effects on a variety of different tissues.

In accordance with one aspect of the present invention, there is provided a novel mature polypeptide, as well as biologically active and diagnostically or therapeutically useful fragments, analogs and derivatives thereof. The polypeptide of the present invention is of human origin.

In accordance with another aspect of the present invention, there are provided isolated nucleic acid molecules encoding a polypeptide of the present invention including mRNAs, DNAS, cDNAs, genomic DNAs as well as analogs and biologically active and diagnostically or therapeutically useful fragments thereof.

In accordance with yet a further aspect of the present invention, there is provided a process for producing such polypeptide by recombinant techniques comprising culturing recombinant prokaryotic and/or eukaryotic host cells, containing a nucleic acid sequence encoding a polypeptide of the present invention, under conditions promoting expression of said protein and subsequent recovery of said protein.

In accordance with yet a further aspect of the present invention, there is provided a process for utilizing such polypeptide, or polynucleotide encoding such polypeptide for therapeutic purposes, for example, enhancing the repair of connective and support tissue, promoting the attachment, fixation and stabilization of tissue implants and enhancing wound healing.

In accordance with yet a further aspect of the present invention, there are provided antibodies against such polypeptides.

In accordance with yet a further aspect of the present invention, there is also provided nucleic acid probes comprising nucleic acid molecules of sufficient length to specifically hybridize to a nucleic acid sequence of the present invention.

In accordance with yet a further aspect of the present invention, there are provided antibodies against such polypeptides.

In accordance with another aspect of the present invention, there are provided agonists which mimic the polypeptide of the present invention and binds to the receptors.

In accordance with yet another aspect of the present invention, there are provided antagonists to such polypeptides, which may be used to inhibit the action of such polypeptides, for example, in the treatment of CTGF dependent tumor growth.

In accordance with still another aspect of the present invention, there are provided diagnostic assays for detecting diseases or susceptibility to diseases related to mutations in the nucleic acid sequences encoding a polypeptide of the present invention.

In accordance with yet a further aspect of the present invention, there is provided a process for utilizing such polypeptides, or polynucleotides encoding such polypeptides, for in vitro purposes related to scientific research, for example, synthesis of DNA and manufacture of DNA vectors.

These and other aspects of the present invention should be apparent to those skilled in the art from the teachings herein.

The following drawings are illustrative of embodiments of the invention and are not meant to limit the scope of the invention as encompassed by the claims.

FIGS. 1a–1c depict the cDNA sequence and corresponding deduced amino acid sequence of CTGF-2. The standard one-letter abbreviation for amino acids is used.

FIGS. 2a–2b are an amino acid comparison between CTGF-2 (top) and Cyr61 ((bottom) illustrating the amino acid sequence homology.

FIG. 3 is an amino acid comparison between CTGF-2 (top) and mouse CTGF (bottom) illustrating the amino acid sequence homology.

In accordance with an aspect of the present invention, there is provided an isolated nucleic acid (polynucleotide) which encodes for the mature polypeptide having the deduced amino acid sequence of FIG. 1 (SEQ ID NO:2) or for the mature polypeptide encoded by the cDNA of the clone deposited as ATCC Deposit No. 75804.

The polynucleotide of this invention was discovered in a cDNA library derived from Human fetal lung. It is structurally related to the IGF and PDGF family. It contains an open reading frame encoding a protein of approximately 381 amino acid residues of which approximately the first 24 amino acids residues are the putative leader sequence such that the putative mature protein comprises 357 amino acids. The protein exhibits the highest degree of homology to Mouse CTGF with 49% identity and 67% similarity and to Cyr61 with 89% identity and 93% similarity. Cyr61 is a growth factor-inducible immediate early gene initially identified in serum-stimulated mouse fibroblasts. It encodes a member of an emerging family of cysteine-rich secreted proteins that includes a connective tissue growth factor (O'Brien and Lau, L. F., Cell Growth Differ., 3:645–54 (1992)).

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 (SEQ ID NO:1) or that of the deposited clone or may be a different coding sequence which coding sequence, as a result of the redundancy or degeneracy of the genetic code, encodes the same mature polypeptide as the DNA of FIG. 1 (SEQ ID NO:1) or the deposited cDNA.

The polynucleotide which encodes for the mature polypeptide of FIG. 1 (SEQ ID NO:2) or for the mature polypeptide encoded by the deposited cDNA may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 (SEQ ID NO:2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 (SEQ ID NO:2) or the same mature polypeptide encoded by the cDNA of the deposited clone as well as variants of such polynucleotides which variants encode for a fragment, derivative or analog of the polypeptide of FIG. 1 (SEQ ID NO:2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 90%, and more preferably at least 95% identity between the sequences. The present invention particularly relates to polynucleotides which hybridize under stringent conditions to the hereinabove-described. polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIG. 1 (SEQ ID NO:1) or the deposited cDNA(s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a polypeptide which has the deduced amino acid sequence of FIG. 1 (SEQ ID NO:2) or which has the amino acid sequence encoded by the deposited cDNA, as well as fragments, analogs and derivatives of such polypeptide.

The terms "fragment," "derivative" and "analog" when referring to the polypeptide of FIG. 1 (SEQ ID NO:2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli*. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli*, Streptomyces, *Salmonella tyhimurium*; fungal cells, such as yeast; insect cells such as Drosophila S2 and Spodoptera Sf9; animal cells such as CHO, COS or Bowes melanoma;

adenoviruses; plant cells; etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia); Eukaryotic: pWLNEO, pSV2CAT, pOG44, pXT1, pSG (Stratagene) pSVK3, pBPV, pMSG, PSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The CTGF-2 polypeptides of the present invention may be employed to enhance the repair of connective and support tissue. For example CTGF-2 may be used to treat skin disorders such as injuries, acne, aging, UV damage or burns. CTGF-2 may also be employed to improve the cosmetic appearance of the skin, for example, by treating wrinkled skin.

CTGF-2 may also be employed to promote the attachment, fixation and stabilization of tissue implants, for example, a prosthesis and other implants inserted during reconstructive surgery. The CTGF-2 polypeptide of the present invention may be employed in the healing of external wounds, by promoting growth of epithelial and connective tissues and the synthesis of total protein and collagen. CTGF-2 may be applied in the area of injured or depleted bones, with regeneration occurring by promoting the growth of connective tissue, bone and cementum and by stimulating protein and collagen synthesis which is especially useful for periodontal disease.

This invention provides a method for identification of the receptor for the CTGF-2 polypeptide. The gene encoding the receptor can be identified by expression cloning. Briefly, polyadenylated RNA is prepared from a cell responsive to CrGF-2, and a cDNA library created from this RNA is divided into pools and used to transfect COS cells or other cells that are not responsive to CTGF-2. Transfected cells which are grown on glass slides are exposed to labeled CrGF-2. The CTGF-2 can be labeled by a variety of means including iodination or inclusion of a recognition site for a site-specific protein kinase. Following fixation and incubation, the slides are subjected to autoradiographic analysis. Positive pools are identified and sub-pools are prepared and retransfected using an iterative sub-pooling and rescreening process, eventually yielding a single clone that encodes the putative receptor. As an alternative approach for receptor identification, labeled ligand can be photoaffinity linked with cell membrane or extract preparations that express the receptor molecule. Cross-linked material is resolved by PAGE and exposed to x-ray film. The labeled complex containing the CTGF-2 receptor can be excised, resolved into peptide fragments, and subjected to protein microsequencing. The amino acid sequence obtained from microsequencing would be used to design a set of generate oligonucleotide probes to screen a cDNA library to identify the gene encoding the putative receptor.

This invention also provides a method of screening compounds to identify those which bind to the CTGF-2 receptor and elicit a second messenger response (agonists) or do not elicit a second messenger response (antagonists). As an example, a mammalian cell or membrane preparation expressing the CTGF-2 receptor would be incubated with a labeled compound. The response of a known second messenger system following interaction of the compound and the CTGF-2 receptor is then measured. Such second messenger systems include but are not limited to, cAMP guanylate cyclase, ion channels or phosphoinositide hydrolysis.

The present invention is also directed to antagonists molecules of the polypeptides of the present invention, and their use in reducing or eliminating the function of CTGF-2.

An example of an antagonist is an antibody or in some cases, an oligonucleotide, which binds to the CTGF-2 polypeptide. Alternatively, antagonists include closely related proteins that have lost biological function and thereby prevent the action of CTGF-2 since receptor sites are occupied.

Antisense technology may be employed to decrease the level of in vivo circulation of CTGF-2. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991), thereby preventing transcription and the production of CTGF-2. The antisense RNA oligonucleotide hybridizes to the mRNA in vivo and blocks translation of the mRNA molecule into CTGF-2 (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of CTGF-2.

Another example of an antagonist is a small molecule which binds to the CTGF-2 receptors such that normal biological activity is prevented. Examples of small molecules include but are not limited to small peptides or peptide-like molecules.

The antagonists may be employed to prevent scar formation due to excess proliferation of connective tissues and to prevent CTGF-2 dependent tumor growth. The antagonists may be employed in a composition with a pharmaceutically acceptable carrier, e.g., as hereinabove described.

The present invention also relates to an assay for identifying potential antagonists specific to CTGF-2. An example of such an assay combines CTGF-2 and a potential antagonist with membrane-bound CTGF-2 receptors or recombinant CTGF-2 under appropriate conditions for a competitive inhibition assay. CTGF-2 can be labeled, such as by radio activity, such that the number of CTGF-2 molecules bound to the receptor can determine the effectiveness of the potential antagonist.

The polypeptides and antagonists and agonists of the present invention may be employed in combination with a suitable pharmaceutical carrier. Such compositions comprise a therapeutically effective amount of the polypeptide, agonist or antagonist, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides, agonists and antagonists of the present invention may be employed in conjunction with other therapeutic compounds.

The pharmaceutical compositions may be administered in a convenient manner such as by the topical, intravenous, intraperitoneal, intramuscular, subcutaneous, intranasal or intradermal routes. CTGF-2 is administered in an amount which is effective for treating and/or prophylaxis of the specific indication. In general, CTGF-2 will be administered in an amount of at least about 10 µg/kg body weight and in most cases CTGF-2 will be administered in an amount not in excess of about 8 mg/Kg body weight per day. In most cases, the dosage is from about 10 µg/kg to about 1 mg/kg body weight daily, taking into account the routes of administration, symptoms, etc.

The polypeptides may also be employed in accordance with the present invention by expression of such polypeptides in viva, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques,* Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide. The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy,* Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

This invention is also related to the use of the gene of the present invention as a diagnostic. Detection of a mutated form of the gene will allow a diagnosis of a disease or a susceptibility to a disease which results from underexpression of CTGF-2.

Individuals carrying mutations in the gene of the present invention may be detected at the DNA level by a variety of techniques. Nucleic acids for diagnosis may be obtained from a patient's cells, including but not limited to blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding CTGF-2 can be used to identify and analyze mutations. For example, deletions and insertions can be detected by a change in size of the amplified product in comparison to the normal genotype. Point mutations can be identified by hybridizing amplified DNA to radiolabeled RNA or alternatively, radiolabeled antisense DNA sequences. Perfectly matched sequences can be distinguished from mismatched duplexes by RNase A digestion or by differences in melting temperatures.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of the polypeptide of the present invention in various tissues since an over-expression of the proteins compared to normal control tissue samples can detect the presence of disorders of the host. Assays used to detect levels of the polypeptide of the present invention in a sample derived from a host are well-known to those of skill in the art and include radioimmunoassays, competitive-binding assays, Western Blot analysis and preferably an ELISA assay. An ELISA assay initially comprises preparing an antibody specific to the CTGF-2 antigen, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now-removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attached to the polypeptide of the present invention attached to the polystyrene dish. All unbound monoclonal antibody is washed out with buffer. The reporter antibody linked to horseradish peroxidase is now placed in the dish resulting in binding of the reporter antibody to any monoclonal antibody bound to the polypeptide of the present invention. Unattached reporter antibody is then washed out. Peroxidase substrates are then added to the dish and the amount of color developed in a given time period is a measurement of the amount of the polypeptide of the present invention present in a given volume of patient sample when compared against a standard curve.

A competition assay may be employed wherein antibodies specific to the polypeptide of the present invention are attached to a solid support and labeled CTGF-2 and a sample derived from the host are passed over the solid support and the amount of label detected attached to the solid support can be correlated to a quantity of the polypeptide of the present invention in the sample.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA having at least 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance-of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Cloning and Expression of CTGF-2 in a Baculovirus Expression System

The DNA sequence encoding the full length CTGF-2 protein, ATCC # 75804, was amplified using PCR oligonucleotide primers corresponding to the 5' and 3' sequences of the gene: The 5' primer has the sequence CGCGGGATC-CTGCGCGACACAATGAGCT (SEQ ID NO:3) and contains a BamHI restriction enzyme site (in bold) followed by 18 nucleotides resembling an efficient signal for the initiation of translation in eukaryotic cells (J. Mol. Biol. 1987, 196, 947–950, Kozak, M.). The initiation codon for translation "ATG" is underlined.

The 3' primer has the sequence CGCGGGTACCAGG-TAGCATTTAGTCCCTAA (SEQ ID NO:4) and contains the cleavage site for the restriction endonuclease Asp781 and 20 nucleotides complementary to the 3' non-translated sequence of the CTGF-2 gene. The amplified sequences were isolated from a 1% agarose gel using a commercially available kit ("Geneclean", BIO 101 Inc., La Jolla, Calif.). The fragment was then digested with the endonucleases BamHI and Asp781 and then purified by isolation on a 1% agarose gel. This fragment is designated F2.

The vector pRG1 (modification of pVL941 vector, discussed below) is used for the expression of the CTGF-2 protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonucleases BamHI and Asp781. The polyadenylation site of the simian virus (SV)40 is used for efficient polyadenylation. For an easy selection of recombinant viruses the beta-galactosidase gene from *E.coli* is inserted in the same orientation as the polyhedrin promoter followed by the polyadenylation signal of the polyhedrin gene. The polyhedrin sequences are flanked at both sides by viral sequences for the cell-mediated homologous recombination of cotransfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid was digested with the restriction enzymes BamHI and Asp781 and then dephosphorylated using calf intestinal phosphatase by procedures known in the art. The DNA was then isolated from a 1% agarose gel. This vector DNA is designated V2.

Fragment F2 and the dephosphorylated plasmid V2 were ligated with T4 DNA ligase. *E.coli* HB101 cells were then transformed and bacteria identified that contained the plasmid (pBacCTGF-2) with the CTGF-2 gene using the enzymes BamHI and Asp781. The sequence of the cloned fragment was confirmed by DNA sequencing.

5 µg of the plasmid pBacCTGF-2 were cotransfected with 1.0 µg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 µg of BaculoGold™ virus DNA and 5 µg of the plasmid pBacCTGF-2 were mixed in a sterile well of a microtiter plate containing 50 µl of serum free Grace's medium (Life Technologies Inc., Gaithersburg, Md.). Afterwards 10 µl Lipofectin plus 90 µl Grace's medium were added, mixed and incubated for 15 minutes at room temperature. Then the transfection mixture was added dropwise to the Sf9 insect cells (ATCC CRL 1711) seeded in a 35 mm tissue culture plate with 1 ml Grace' medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution of the viruses was added to the cells, blue stained plaques were picked with the tip of an Eppendorf pipette. The agar containing the recombinant viruses was then resuspended in an Eppendorf tube containing 200 µl of Grace's medium. The agar was removed by a brief centrifugation and the supernatant containing the recombinant baculoviruses was used to insect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-CTGF-2 at a multiplicity of infection (MOI) of 2. Six hours later the medium was removed and replaced with SF900 II medium minus methionine and cysteine (Life Technologies Inc., Gaithersburg). 42 hours later 5 µCi of $^{35}$S-methionine and 5 µCi $^{35}$S cysteine (Amersham) were added. The cells were further incubated for 16 hours before they were harvested by centrifugation and the labelled proteins visualized by SDS-PAGE and autoradiography.

EXAMPLE 2

Expression of Recombinant CTGF-2 in COS Cells

The expression of plasmid, CTGF-2 HA is derived from a vector pcDNAI/Amp (Invitrogen) containing: 1) SV40 origin of replication, 2) ampicillin resistance gene, 3) *E.coli* replication origin, 4) CMV promoter followed by a polylinker region, a SV40 intron and polyadenylation site. A DNA fragment encoding the entire CTGF-2 precursor and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to our target protein allows easy detection of the recombinant protein with an antibody that recognizes the HA epitope.

The plasmid construction strategy is described as follows:

The DNA sequence encoding for CTGF-2, ATCC # 75804, was constructed by PCR on the full-length clone using two primers: the 5' primer 5' AAAGGATCCACAAT-GAGCTCCCGAATC (SEQ ID NO:5) 3' contains a Bam HI site followed by 18 nucleotides of CTGF-2 coding sequence starting from the −3 position relative to the initiation codon; the 3' sequence 5' CGCTCTAGATTAAGCGTAGTCTGG-GACGTCGTATGGGTATTGGAACAGCCTGTAGAAG 5' (SEQ ID NO:6) contains complementary sequences to an Xba I site, translation stop codon, HA tag and the last 19 nucleotides of the CTGF-2 coding sequence (not including the stop codon). Therefore, the PCR product contains a Bam HI site, CTGF-2 coding sequence followed by an HA tag fused in frame, a translation termination stop codon next to the HA tag, and an Xba I site. The PCR amplified DNA fragment and the vector, pcDNAI/Amp, were digested with Bam HI and Xba I restriction enzymes and ligated. The ligation mixture was transformed into *E. coli* strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant CTGF-2, COS cells were transfected with the expression vector by DEAE-DEXTRAN method. (J. Sambrook, E. Fritsch, T. Maniatis, Molecular Cloning: A Laboratory Manual, Cold Spring Laboratory Press, (1989)). The expression of the CTGF-2 HA protein was detected by radiolabelling and immunoprecipitation method. (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5). (Wilson, I. et al., Id. 37:767 (1984)). Both cell lysate and culture media were precipitated with a HA specific monoclonal antibody. Proteins precipitated were analyzed on 15% SDS-PAGE gels.

EXAMPLE 3

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

---

What is claimed is:

1. An isolated polypeptide comprising an amino acid sequence selected from the group consisting of:
   (a) amino acids 1 to 381 of SEQ ID NO:2;
   (b) amino acids 2 to 381 of SEQ ID NO:2;
   (c) amino acids 25 to 381 of SEQ ID NO:2; and
   (d) a polypeptide fragment of SEQ ID NO:2, wherein said fragment stimulates cellular proliferation.

2. The polypeptide of claim 1, wherein said amino acid sequence is (a).

3. The polypeptide of claim 2, wherein the amino acid sequence is fused to a heterologous polypeptide.

4. The polypeptide of claim 1, wherein said amino acid sequence is (b).

5. The polypeptide of claim 4, wherein the amino acid sequence is fused to a heterologous polypeptide.

6. The polypeptide of claim 1, wherein said amino acid sequence is (c).

7. The polypeptide of claim 6, wherein the amino acid sequence is fused to a heterologous polypeptide.

8. The polypeptide of claim 1, wherein said amino acid sequence is (d).

9. The polypeptide of claim 8, wherein the amino acid sequence is fused to a heterologous polypeptide.

10. The polypeptide of claim 2, wherein the amino acid sequence is fused to a heterologous polypeptide.

11. An isolated polypeptide comprising a first amino acid sequence that is at least 95% identical to a second amino acid sequence selected from the group consisting of:

(a) amino acids 1 to 381 of SEQ ID NO:2;

(b) amino acids 2 to 381 of SEQ ID NO:2;

(c) amino acids 25 to 381 of SEQ ID NO:2; and (d) a polypeptide fragment of SEQ ID NO:2, wherein said polypeptide or polypeptide fragment stimulates cellular proliferation.

12. The polypeptide of claim 11, wherein said second amino acid sequence is (a).

13. The polypeptide of claim 12, wherein the amino acid sequence is fused to a heterologous polypeptide.

14. The polypeptide of claim 11, wherein said second amino acid sequence is (b).

15. The polypeptide of claim 14, wherein the amino acid sequence is fused to a heterologous polypeptide.

16. The polypeptide of claim 11, wherein said second amino acid sequence is (c).

17. The polypeptide of claim 16, wherein the amino acid sequence is fused to a heterologous polypeptide.

18. The polypeptide of claim 11, wherein said second amino acid sequence is (d).

19. The polypeptide of claim 18, wherein the amino acid sequence is fused to a heterologous polypeptide.

20. An isolated polypeptide comprising an amino acid sequence selected from the group consisting of:

(a) the amino acid sequence of the full-length polypeptide encoded by the human cDNA contained in ATCC Deposit Number 75804;

(b) the amino acid sequence of the full-length polypeptide, lacking the N-terminal methionine, encoded by the human cDNA contained in ATCC Deposit Number 75804;

(c) the amino acid sequence of the mature polypeptide encoded by the human cDNA contained in ATCC Deposit Number 75804; and (d) a polypeptide fragment of the polypeptide encoded by the human cDNA contained in ATCC Deposit Number 75804, wherein said fragment stimulates cellular proliferation.

21. The polypeptide of claim 20, wherein said amino acid sequence is (a).

22. The polypeptide of claim 21, wherein the amino acid sequence is fused to a heterologous polypeptide.

23. The polypeptide of claim 20, wherein said amino acid sequence is (b).

24. The polypeptide of claim 23, wherein the amino acid sequence is fused to a heterologous polypeptide.

25. The polypeptide of claim 20, wherein said amino acid sequence is (c).

26. The polypeptide of claim 25, wherein the amino acid sequence is fused to a heterologous polypeptide.

27. The polypeptide of claim 20, wherein said amino acid sequence is (d).

28. The polypeptide of claim 27, wherein the amino acid sequence is fused to a heterologous polypeptide.

29. An isolated polypeptide comprising a first amino acid sequence that is at least 95% identical to a second amino acid sequence selected from the group consisting of:

(a) the amino acid sequence of the full-length polypeptide encoded by the human cDNA contained in ATCC Deposit Number 75904;

(b) the amino acid sequence of the full-length polypeptide, lacking the N-terminal methionine, encoded by the human cDNA contained in ATCC Deposit Number 75904;

(c) the amino acid sequence of the mature polypeptide encoded by the human cDNA contained in ATCC Deposit Number 75904; and (d) a polypeptide fragment of the polypeptide encoded by the human cDNA contained in ATCC Deposit Number 75904;

wherein said polypeptide or polypeptide fragment stimulates cellular proliferation.

30. The polypeptide of claim 29, wherein said second amino acid sequence is (a).

31. The polypeptide of claim 30, wherein the amino acid sequence is fused to a heterologous polypeptide.

32. The polypeptide of claim 29, wherein said second amino acid sequence is (b).

33. The polypeptide of claim 32, wherein the amino acid sequence is fused to a heterologous polypeptide.

34. The polypeptide of claim 29, wherein said second amino acid sequence is (c).

35. The polypeptide of claim 34, wherein the amino acid sequence is fused to a heterologous polypeptide.

36. The polypeptide of claim 29, wherein said second amino acid sequence is (d).

37. The polypeptide of claim 36, wherein the amino acid sequence is fused to a heterologous polypeptide.

* * * * *

UNITED STATES PATENT AND TRADEMARK OFFICE
CERTIFICATE OF CORRECTION

PATENT NO. : 6,534,630 B1
APPLICATION NO. : 09/348815
DATED : March 18, 2003
INVENTOR(S) : Li et al.

It is certified that error appears in the above-identified patent and that said Letters Patent is hereby corrected as shown below:

On the Title Page: Item (62)

Delete the paragraph under "Related U. S. Application Data" and replace it with the following:

-- Division of application No. 08/459,101, filed June 2, 1995, which is a continuation-in-part of application No. PCT/US94/07736, filed July 12, 1994, now Pat. No. 5,945,300. --

In the Figures:

Delete Drawing Sheet 1-5 and substitute therefor the Drawing sheets consisting of FIG 1A-1C as shown on the attached page.

In the Claims:

Col 28 Lines 16-17; 20-21; 23-24; 26-27

In Claim 29(a), (b), (c) and (d), delete "ATCC Deposit Number 75904" and insert -- ATCC Deposit Number 75804. --

Signed and Sealed this

Nineteenth Day of September, 2006

JON W. DUDAS
*Director of the United States Patent and Trademark Office*

```
  1 ATGAGCTCCCGCATCGCCAGGGCGCTCGCCTTAGTCGTCACCCTTCTCCACTTGACCAGG   60
  1   M   S   S   R   I   A   R   A   L   A   L   V   V   T   L   L   H   L   T   R    20

61 CTGGCGCTCTCCACCTGCCCCGCTGCCTGCCACTGCCCCCTGGAGGCGCCCAAGTGCGCG  120
 21   L   A   L   S   T   C   P   A   A   C   H   C   P   L   E   A   P   K   C   A    40

121 CCGGGAGTCGGGCTGGTCCGGGACGGCTGCGGCTGCTGTAAGGTCTGCGCCAAGCAGCTC  180
 41   P   G   V   G   L   V   R   D   G   C   G   C   C   K   V   C   A   K   Q   L    60

181 AACGAGGACTGCAGCAAAACGCAGCCCTGCGACCACACCAAGGGGCTGGAATGCAACTTC  240
 61   N   E   D   C   S   K   T   Q   P   C   D   H   T   K   G   L   E   C   N   F    80

241 GGCGCCAGCTCCACCGCTCTGAAGGGGATCTGCAGAGCTCAGTCAGAGGGCAGACCCTGT  300
 81   G   A   S   S   T   A   L   K   G   I   C   R   A   Q   S   E   G   R   P   C   100

301 GAATATAACTCCAGAATCTACCAAAACGGGGAAAGTTTCCAGCCCAACTGTAAACATCAG  360
101   E   Y   N   S   R   I   Y   Q   N   G   E   S   F   Q   P   N   C   K   H   Q   120

361 TGCACATGTATTGATGGCGCCGTGGGCTGCATTCCTCTGTGTCCCCAAGAACTATCTCTC  420
121   C   T   C   I   D   G   A   V   G   C   I   P   L   C   P   Q   E   L   S   L   140

421 CCCAACTTGGGCTGTCCCAACCCTCGGCTGGTCAAAGTTACCGGGCAGTGCTGCGAGGAG  480
141   P   N   L   G   C   P   N   P   R   L   V   K   V   T   G   Q   C   C   E   E   160
```

FIG. 1A

```
481  TGGGTCTGTGACGAGGATAGTATCAAGGACCCCATGGAGGACCAGGACGGCCTCCTTGGC  540
161   W   V   C   D   E   D   S   I   K   D   P   M   E   D   Q   D   G   L   L   G   180

541  AAGGAGCTGGGATTCGATGCCTCCGAGGTGGAGTTGACGAGAAACAATGAATTGATTGCA  600
181   K   E   L   G   F   D   A   S   E   V   E   L   T   R   N   N   E   L   I   A   200

601  GTTGGAAAAGGCAGCTCACTGAAGCGGCTCCCTGTTTTTGGAATGGAGCCTCGCATCCTA  660
201   V   G   K   G   S   S   L   K   R   L   P   V   F   G   M   E   P   R   I   L   220

661  TACAACCCTTTACAAGGCCAGAAATGTATTGTTCAAACAACTTCATGGTCCCAGTGCTCA  720
221   Y   N   P   L   Q   G   Q   K   C   I   V   Q   T   T   S   W   S   Q   C   S   240

721  AAGACCTGTGGAACTGGTATCTCCACACGAGTTACCAATGACAACCCTGAGTGCCGCCTT  780
241   K   T   C   G   T   G   I   S   T   R   V   T   N   D   N   P   E   C   R   L   260

781  GTGAAAGAAACCCGGATTTGTGAGGTGCGGCCTTGTGGACAGCCAGTGTACAGCAGCCTG  840
261   V   K   E   T   R   I   C   E   V   R   P   C   G   Q   P   V   Y   S   S   L   280

841  AAAAAGGGCAAGAAATGCAGCAAGACCAAGAAATCCCCCGAACCAGTCAGGTTTACTTAC  900
281   K   K   G   K   K   C   S   K   T   K   K   S   P   E   P   V   R   F   T   Y   300

901  GCTGGATGTTTGAGTGTGAAGAAATACCGGCCCAAGTACTGCGGTTCCTGCGTGGACGGC  960
301   A   G   C   L   S   V   K   K   Y   R   P   K   Y   C   G   S   C   V   D   G   320
```

FIG. 1B

```
 961  CGATGCTGCACGCCCCAGCTGACCAGGACTGTGAAGATGCGGTTCCGCTGCGAAGATGGG  1020
 321   R  C  C  T  P  Q  L  T  R  T  V  K  M  R  F  R  C  E  D  G   340

1021  GAGACATTTTCCAAGAACGTCATGATGATCCAGTCCTGCAAATGCAACTACAACTGCCCG  1080
 341   E  T  F  S  K  N  V  M  M  I  Q  S  C  K  C  N  Y  N  C  P   360

1081  CATGCCAATGAAGCAGCGTTTCCCTTCTACAGGCTGTTCAATGACATTCACAAATTTAGG  1140
 361   H  A  N  E  A  A  F  P  F  Y  R  L  F  N  D  I  H  K  F  R   380

1141  GACTAA  1146
 381   D  *   382
```

FIG. 1C

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH: 1146 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 1..1146

(xi) SEQUENCE DESCRIPTION: SEQ ID NO: 1:

```
ATG AGC TCC CGC ATC GCC AGG GCG CTC GCC TTA GTC GTC ACC CTT CTC        48
Met Ser Ser Arg Ile Ala Arg Ala Leu Ala Leu Val Val Thr Leu Leu
 1               5                  10                  15

CAC TTG ACC AGG CTG GCG CTC TCC ACC TGC CCC GCT GCC TGC CAC TGC        96
His Leu Thr Arg Leu Ala Leu Ser Thr Cys Pro Ala Ala Cys His Cys
             20                  25                  30

CCC CTG GAG GCG CCC AAG TGC GCG CCG GGA GTC GGG CTG GTC CGG GAC       144
Pro Leu Glu Ala Pro Lys Cys Ala Pro Gly Val Gly Leu Val Arg Asp
         35                  40                  45

GGC TGC GGC TGC TGT AAG GTC TGC GCC AAG CAG CTC AAC GAG GAC TGC       192
Gly Cys Gly Cys Cys Lys Val Cys Ala Lys Gln Leu Asn Glu Asp Cys
     50                  55                  60

AGC AAA ACG CAG CCC TGC GAC CAC ACC AAG GGG CTG GAA TGC AAC TTC       240
Ser Lys Thr Gln Pro Cys Asp His Thr Lys Gly Leu Glu Cys Asn Phe
 65                  70                  75                  80

GGC GCC AGC TCC ACC GCT CTG AAG GGG ATC TGC AGA GCT CAG TCA GAG       288
```

```
Gly Ala Ser Ser Thr Ala Leu Lys Gly Ile Cys Arg Ala Gln Ser Glu
                85                  90                  95

GGC AGA CCC TGT GAA TAT AAC TCC AGA ATC TAC CAA AAC GGG GAA AGT        336
Gly Arg Pro Cys Glu Tyr Asn Ser Arg Ile Tyr Gln Asn Gly Glu Ser
            100                 105                 110

TTC CAG CCC AAC TGT AAA CAT CAG TGC ACA TGT ATT GAT GGC GCC GTG        384
Phe Gln Pro Asn Cys Lys His Gln Cys Thr Cys Ile Asp Gly Ala Val
            115                 120                 125

GGC TGC ATT CCT CTG TGT CCC CAA GAA CTA TCT CTC CCC AAC TTG GGC        432
Gly Cys Ile Pro Leu Cys Pro Gln Glu Leu Ser Leu Pro Asn Leu Gly
        130                 135                 140

TGT CCC AAC CCT CGG CTG GTC AAA GTT ACC GGG CAG TGC TGC GAG GAG        480
Cys Pro Asn Pro Arg Leu Val Lys Val Thr Gly Gln Cys Cys Glu Glu
145                 150                 155                 160

TGG GTC TGT GAC GAG GAT AGT ATC AAG GAC CCC ATG GAG GAC CAG GAC        528
Trp Val Cys Asp Glu Asp Ser Ile Lys Asp Pro Met Glu Asp Gln Asp
                165                 170                 175

GGC CTC CTT GGC AAG GAG CTG GGA TTC GAT GCC TCC GAG GTG GAG TTG        576
Gly Leu Leu Gly Lys Glu Leu Gly Phe Asp Ala Ser Glu Val Glu Leu
            180                 185                 190

ACG AGA AAC AAT GAA TTG ATT GCA GTT GGA AAA GGC AGC TCA CTG AAG        624
Thr Arg Asn Asn Glu Leu Ile Ala Val Gly Lys Gly Ser Ser Leu Lys
            195                 200                 205

CGG CTC CCT GTT TTT GGA ATG GAG CCT CGC ATC CTA TAC AAC CCT TTA        672
Arg Leu Pro Val Phe Gly Met Glu Pro Arg Ile Leu Tyr Asn Pro Leu
        210                 215                 220

CAA GGC CAG AAA TGT ATT GTT CAA ACA ACT TCA TGG TCC CAG TGC TCA        720
Gln Gly Gln Lys Cys Ile Val Gln Thr Thr Ser Trp Ser Gln Cys Ser
225                 230                 235                 240

AAG ACC TGT GGA ACT GGT ATC TCC ACA CGA GTT ACC AAT GAC AAC CCT        768
Lys Thr Cys Gly Thr Gly Ile Ser Thr Arg Val Thr Asn Asp Asn Pro
                245                 250                 255

GAG TGC CGC CTT GTG AAA GAA ACC CGG ATT TGT GAG GTG CGG CCT TGT        816
Glu Cys Arg Leu Val Lys Glu Thr Arg Ile Cys Glu Val Arg Pro Cys
            260                 265                 270

GGA CAG CCA GTG TAC AGC AGC CTG AAA AAG GGC AAG AAA TGC AGC AAG        864
Gly Gln Pro Val Tyr Ser Ser Leu Lys Lys Gly Lys Lys Cys Ser Lys
            275                 280                 285

ACC AAG AAA TCC CCC GAA CCA GTC AGG TTT ACT TAC GCT GGA TGT TTG        912
Thr Lys Lys Ser Pro Glu Pro Val Arg Phe Thr Tyr Ala Gly Cys Leu
        290                 295                 300

AGT GTG AAG AAA TAC CGG CCC AAG TAC TGC GGT TCC TGC GTG GAC GGC        960
Ser Val Lys Lys Tyr Arg Pro Lys Tyr Cys Gly Ser Cys Val Asp Gly
305                 310                 315                 320

CGA TGC TGC ACG CCC CAG CTG ACC AGG ACT GTG AAG ATG CGG TTC CGC       1008
Arg Cys Cys Thr Pro Gln Leu Thr Arg Thr Val Lys Met Arg Phe Arg
                325                 330                 335

TGC GAA GAT GGG GAG ACA TTT TCC AAG AAC GTC ATG ATG ATC CAG TCC       1056
Cys Glu Asp Gly Glu Thr Phe Ser Lys Asn Val Met Met Ile Gln Ser
            340                 345                 350

TGC AAA TGC AAC TAC AAC TGC CCG CAT GCC AAT GAA GCA GCG TTT CCC       1104
Cys Lys Cys Asn Tyr Asn Cys Pro His Ala Asn Glu Ala Ala Phe Pro
            355                 360                 365

TTC TAC AGG CTG TTC AAT GAC ATT CAC AAA TTT AGG GAC TAA              1146
Phe Tyr Arg Leu Phe Asn Asp Ile His Lys Phe Arg Asp
        370                 375                 380

(2) INFORMATION FOR SEQ ID NO: 2:

(i) SEQUENCE CHARACTERISTICS:
```

(A) LENGTH: 381 amino acids
(B) TYPE: amino acid
(D) TOPOLOGY: linear (ii) MOLECULE TYPE: protein (xi) SEQUENCE DESCRIPTION: SEQ ID NO: 2:

```
Met Ser Ser Arg Ile Ala Arg Ala Leu Ala Leu Val Val Thr Leu Leu
 1               5                  10                  15

His Leu Thr Arg Leu Ala Leu Ser Thr Cys Pro Ala Ala Cys His Cys
             20                  25                  30

Pro Leu Glu Ala Pro Lys Cys Ala Pro Gly Val Gly Leu Val Arg Asp
         35                  40                  45

Gly Cys Gly Cys Cys Lys Val Cys Ala Lys Gln Leu Asn Glu Asp Cys
     50                  55                  60

Ser Lys Thr Gln Pro Cys Asp His Thr Lys Gly Leu Glu Cys Asn Phe
 65                  70                  75                  80

Gly Ala Ser Ser Thr Ala Leu Lys Gly Ile Cys Arg Ala Gln Ser Glu
                 85                  90                  95

Gly Arg Pro Cys Glu Tyr Asn Ser Arg Ile Tyr Gln Asn Gly Glu Ser
            100                 105                 110

Phe Gln Pro Asn Cys Lys His Gln Cys Thr Cys Ile Asp Gly Ala Val
        115                 120                 125

Gly Cys Ile Pro Leu Cys Pro Gln Glu Leu Ser Leu Pro Asn Leu Gly
    130                 135                 140

Cys Pro Asn Pro Arg Leu Val Lys Val Thr Gly Gln Cys Cys Glu Glu
145                 150                 155                 160

Trp Val Cys Asp Glu Asp Ser Ile Lys Asp Pro Met Glu Asp Gln Asp
                165                 170                 175

Gly Leu Leu Gly Lys Glu Leu Gly Phe Asp Ala Ser Glu Val Glu Leu
            180                 185                 190

Thr Arg Asn Asn Glu Leu Ile Ala Val Gly Lys Gly Ser Ser Leu Lys
        195                 200                 205

Arg Leu Pro Val Phe Gly Met Glu Pro Arg Ile Leu Tyr Asn Pro Leu
    210                 215                 220

Gln Gly Gln Lys Cys Ile Val Gln Thr Thr Ser Trp Ser Gln Cys Ser
225                 230                 235                 240

Lys Thr Cys Gly Thr Gly Ile Ser Thr Arg Val Thr Asn Asp Asn Pro
                245                 250                 255

Glu Cys Arg Leu Val Lys Glu Thr Arg Ile Cys Glu Val Arg Pro Cys
            260                 265                 270

Gly Gln Pro Val Tyr Ser Ser Leu Lys Lys Gly Lys Lys Cys Ser Lys
        275                 280                 285

Thr Lys Lys Ser Pro Glu Pro Val Arg Phe Thr Tyr Ala Gly Cys Leu
    290                 295                 300

Ser Val Lys Lys Tyr Arg Pro Lys Tyr Cys Gly Ser Cys Val Asp Gly
305                 310                 315                 320

Arg Cys Cys Thr Pro Gln Leu Thr Arg Thr Val Lys Met Arg Phe Arg
                325                 330                 335

Cys Glu Asp Gly Glu Thr Phe Ser Lys Asn Val Met Met Ile Gln Ser
            340                 345                 350

Cys Lys Cys Asn Tyr Asn Cys Pro His Ala Asn Glu Ala Ala Phe Pro
        355                 360                 365

Phe Tyr Arg Leu Phe Asn Asp Ile His Lys Phe Arg Asp
    370                 375                 380
```

(2) INFORMATION FOR SEQ ID NO: 3:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

CGCGGGATCC TGCGCGACAC AATGAGCT          28

(2) INFORMATION FOR SEQ ID NO: 4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

CGCGGGTACC AGGTAGCATT TAGTCCCTAA        30

(2) INFORMATION FOR SEQ ID NO: 5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

AAAGGATCCA CAATGAGCTC CCGAATC          27

(2) INFORMATION FOR SEQ ID NO: 6:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

CGCTCTAGAT TAAGCGTAGT CTGGGACGTC GTATGGGTAT TGGAACAGCC TGTAGAAG    58